United States Patent
Lin et al.

(10) Patent No.: US 11,782,030 B2
(45) Date of Patent: Oct. 10, 2023

(54) CLAMPING APPARATUS FOR ULTRASONIC DETECTION DEVICE

(71) Applicant: NATIONAL TAIPEI UNIVERSITY OF TECHNOLOGY, Taipei (TW)

(72) Inventors: Hsien-I Lin, Taipei (TW); Ching-Hui Yen, Taipei (TW)

(73) Assignee: NATIONAL TAIPEI UNIVERSITY OF TECHNOLOGY, Taipei (TW)

(*) Notice: Subject to any disclaimer, the term of this patent is extended or adjusted under 35 U.S.C. 154(b) by 83 days.

(21) Appl. No.: 17/574,603

(22) Filed: Jan. 13, 2022

(65) Prior Publication Data

US 2023/0221287 A1    Jul. 13, 2023

(51) Int. Cl.
*G01N 29/22*    (2006.01)

(52) U.S. Cl.
CPC .................................. *G01N 29/225* (2013.01)

(58) Field of Classification Search
CPC ...... G01N 29/225; G01N 29/22; G01N 29/26; G01N 29/265; G01D 11/30; G01B 5/28; G01B 11/30; G01Q 60/24
USPC ........................ 73/866.5, 816, 593, 104–105
See application file for complete search history.

(56) References Cited

U.S. PATENT DOCUMENTS

2009/0275836 A1* 11/2009 Fujii ..................... A61B 8/483
                                                                    600/459

FOREIGN PATENT DOCUMENTS

| CN | 112213389 A | * | 1/2021 | ............. G01N 29/04 |
| CN | 112450977 A | * | 3/2021 | ............. A61B 5/0095 |
| CN | 213665369 U | * | 7/2021 | ............. A61B 8/00 |
| CN | 113267569 A | * | 8/2021 | ............. G01N 29/26 |
| KR | 100820764 B1 | * | 4/2008 | ............. G01N 29/04 |

* cited by examiner

*Primary Examiner* — Herbert K Roberts
*Assistant Examiner* — Anthony W Megna Fuentes
(74) *Attorney, Agent, or Firm* — Chih Feng Yeh; Huntington IP Consulting Co., Ltd.

(57) ABSTRACT

A clamping apparatus for an ultrasonic detection device is disclosed. A remote control device for remotely controlling a first motor to control a rotational position of a base. The remote control device for remotely controlling a second motor to control a moving position of a movable base relative to a first arc-shaped rack. The remote control device for remotely controlling a third motor to control a moving position of a second arc-shaped rack relative to the movable base, so as to achieve the technical effect of providing an accurate three-dimensional detection angle to the ultrasonic detection device.

10 Claims, 7 Drawing Sheets

CLAMPING APPARATUS FOR ULTRASONIC DETECTION DEVICE

BACKGROUND

1. Technical Field

The present invention is related to a clamping apparatus, and more particularly to a clamping apparatus capable of providing an accurate three-dimensional detection angle to an ultrasonic detection device.

2. Related Art

A modern medical institution has a variety of medical equipment, such as X-ray equipment, electrocardiogram equipment, ultrasound detection equipment and so on. In order to operate the ultrasound detection equipment, a physician needs to hold an ultrasonic detection device to perform ultrasonic detection; the ultrasound detection is a fan-shaped imaging technology, so the physician needs to rotate and swing the ultrasonic detection device in three-dimensional to obtain a detection result. Therefore, conventional ultrasonic detection equipment is inconvenient in operation.

According to the above-mentioned contents, what is needed is to develop an improved technical solution to solve the conventional technology that the conventional ultrasonic detection equipment is inconvenient in operation.

SUMMARY

An objective of the present invention is to disclose a clamping apparatus for an ultrasonic detection device, so as to solve the conventional technology problem that the conventional ultrasonic detection equipment is inconvenient in operation.

In order to achieve the objective of the present invention, the present invention provides a clamping apparatus for an ultrasonic detection device, and the clamping apparatus includes a clamping device and a remote control device. The clamping device includes a base, a first arc-shaped rack, a movable base, a second arc-shaped rack, a first motor, a second motor, a third motor, a first clamping rod and a second clamping rod. The base includes a motor fixing part and a base fixing part. The first arc-shaped rack includes a rack fixing part, a set of first guiding grooves, and a first rack, wherein the rack fixing part is fixed with the base fixing part, and the first rack is disposed on an inner side of the first arc-shaped rack. The movable base includes a rail part and a guiding groove part, wherein the rail part is disposed in perpendicular to the guiding groove part, the rail part includes a rail disposed on a top of the movable base, the guiding groove part includes a second guiding groove disposed on a bottom of the movable base, and the rail part is assembled with the first guiding grooves. The second arc-shaped rack includes a second rack disposed on an inner side thereof, wherein the second arc-shaped rack is assembled with the second guiding groove. The first motor is fixed on the motor fixing part. The second motor includes a second gear, wherein the second motor is fixed on the rail part, and the second gear is assembled with the first rack. The third motor includes a third gear, wherein the third motor is fixed on the guiding groove part, and the third gear is assembled with the second rack. The first clamping rod includes a first fixing end and a first clamping assembly, wherein the first fixing end is fixed on a first end of the second arc-shaped rack. The second clamping rod includes a second fixing end and a second clamping assembly, wherein the second fixing end is fixed on a first end of the second arc-shaped rack. The first clamping assembly and the second clamping assembly are configured to clamp the ultrasonic detection device. The remote control device is configured to remotely control the first motor to control a rotational position of the base, remotely control the second motor to control a moving position of the movable base relative to the first arc-shaped rack, and remotely control the third motor to control a moving position of the second arc-shaped rack relative to the movable base, so as to provide an accurate three-dimensional detection angle to the ultrasonic detection device.

According to an embodiment of the clamping apparatus of the present invention, a perpendicular bisector of the base passes through a central point of a front edge of the ultrasonic detection device.

According to an embodiment of the clamping apparatus of the present invention, a central position of the first arc-shaped rack is at a central point of a front edge of the ultrasonic detection device.

According to an embodiment of the clamping apparatus of the present invention, a central position of the second arc-shaped rack is at a central point of a front edge of the ultrasonic detection device.

According to an embodiment of the clamping apparatus of the present invention, the ultrasonic detection device is assembled with the first clamping assembly and the second clamping assembly by a screwing manner, so as to be clamped between the first clamping assembly and the second clamping assembly.

According to an embodiment of the clamping apparatus of the present invention, the second motor is fixed on the rail part by a screwing manner.

According to an embodiment of the clamping apparatus of the present invention, the third motor is fixed on the guiding groove part by a screwing manner.

According to an embodiment of the clamping apparatus of the present invention, a height of the guiding groove part is greater than a height of the rail part.

According to an embodiment of the clamping apparatus of the present invention, an end of the rail part protruded out of the guiding groove part is configured to fix with the second motor, and the end has an opening formed on a bottom thereof and corresponding in position to the first rack, and the second gear is assembled with the first rack through the opening.

According to an embodiment of the clamping apparatus of the present invention, an end of the guiding groove part protruded out of the rail part is configured to fix with the third motor, and the end has an opening formed on a bottom thereof and corresponding in position to the second rack, and the third gear is assembled with the second rack through the opening.

According to the above-mentioned clamping apparatus of the present invention, the difference between the present invention and the conventional technology is that the remote control device of the clamping apparatus of the present invention is used for remotely controlling the first motor to control the rotational position of the base, for remotely controlling the second motor to control the moving position of the movable base relative to the first arc-shaped rack, and for remotely controlling the third motor to control the moving position of the second arc-shaped rack relative to the movable base.

Therefore, the technical solution of the present invention is able to achieve the technical effect of providing the accurate three-dimensional detection angle to the ultrasonic detection device.

BRIEF DESCRIPTION OF THE DRAWINGS

The structure, operating principle and effects of the present invention will be described in detail by way of various embodiments which are illustrated in the accompanying drawings.

DETAILED DESCRIPTION

Figure 1:
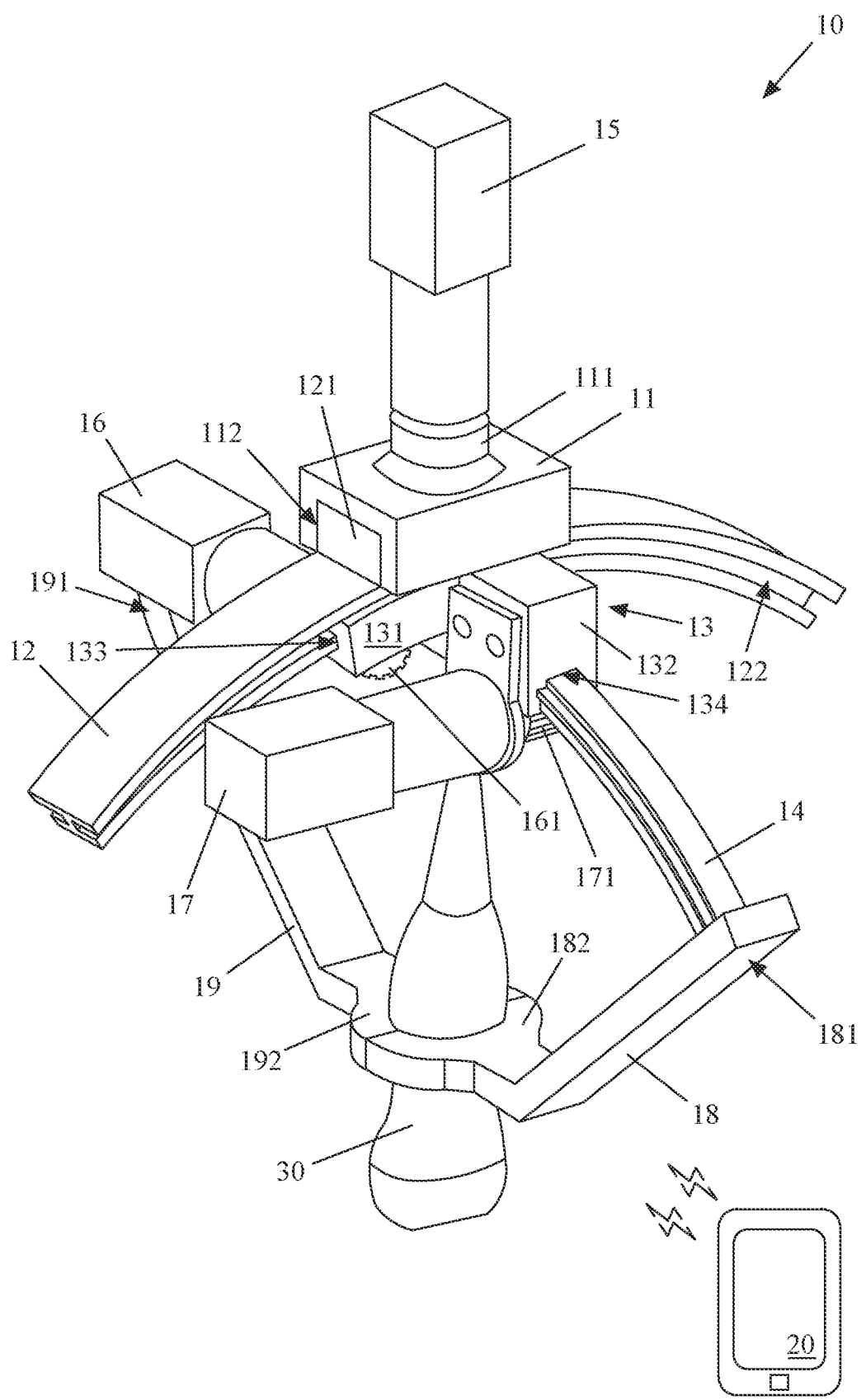
FIG. 1 is a perspective assembled view of a clamping apparatus for an ultrasonic detection device, according to the present invention.

The following embodiments of the present invention are herein described in detail with reference to the accompanying drawings. These drawings show specific examples of the embodiments of the present invention. These embodiments are provided so that this disclosure will be thorough and complete, and will fully convey the scope of the invention to those skilled in the art. It is to be acknowledged that these embodiments are exemplary implementations and are not to be construed as limiting the scope of the present invention in any way. Further modifications to the disclosed embodiments, as well as other embodiments, are also included within the scope of the appended claims.

These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts. As used herein, the singular forms "a", "an" and "the" are intended to include the plural forms as well, unless the context clearly indicates otherwise.

It is to be acknowledged that, although the terms 'first', 'second', 'third', and so on, may be used herein to describe various elements, these elements should not be limited by these terms. These terms are used only for the purpose of distinguishing one component from another component. Thus, a first element discussed herein could be termed a second element without altering the description of the present disclosure. As used herein, the term "or" includes any and all combinations of one or more of the associated listed items.

It will be acknowledged that when an element or layer is referred to as being "on," "connected to" or "coupled to" another element or layer, it can be directly on, connected or coupled to the other element or layer, or intervening elements or layers may be present. In contrast, when an element is referred to as being "directly on," "directly connected to" or "directly coupled to" another element or layer, there are no intervening elements or layers present.

In addition, unless explicitly described to the contrary, the words "comprise" and "include", and variations such as "comprises", "comprising", "includes", or "including", will be acknowledged to imply the inclusion of stated elements but not the exclusion of any other elements.

An embodiment of a clamping apparatus of the present invention will be described in the following paragraphs with reference to figures. Please refer to FIG. 1, which is a perspective assembled view of a clamping apparatus for an ultrasonic detection device, according to the present invention.

As shown in FIG. 1, the clamping apparatus of the present invention includes a clamping device 10 and a remote control device 20, the clamping device 10 includes a base 11, a first arc-shaped rack 12, a movable base 13, a second arc-shaped rack 14, a first motor 15, a second motor 16, a third motor 17, a first clamping rod 18, and a second clamping rod 19. As shown in FIG. 1, a smartphone is taken as a schematic example of the remote control device 20, but the present invention is not limited thereto; in actual application, the remote control device 20 can be implemented by an electronic device with a wireless transmission function, such as a computer, a notebook computer or a tablet computer.

The base 11 of the clamping device 10 includes a motor fixing part 111 and a base fixing part 112, the base 11 of the clamping device 10 can be made by ceramic or polymer; however, these examples are merely for exemplary illustration, and the application field of the present invention is not limited thereto. The motor fixing part 111 of the base 11 is configured to fix with the first motor 15, and the base fixing part 112 of the base 11 is configured to fix with the first arc-shaped rack 12 of the clamping device 10.

The first arc-shaped rack 12 of the clamping device 10 includes a rack fixing part 121, a set of first guiding grooves 122, and a first rack 123. The first arc-shaped rack 12 of the clamping device 10 can be made by ceramic or polymer, but these examples are merely for exemplary illustration, and the application field of the present invention is not limited thereto. The rack fixing part 121 of the first arc-shaped rack 12 is fixed with the base fixing part 112 of the base 11 by a screwing manner, and the first rack 123 of the first arc-shaped rack 12 is disposed on an inner side of the first arc-shaped rack 12.

The movable base 13 of the clamping device 10 can include a rail part 131 and a guiding groove part 132. The movable base 13 of the clamping device 10 can be made by ceramic or polymer, but these examples are merely for exemplary illustration, and the application field of the present invention is not limited thereto. The rail part 131 of the movable base 13 is disposed in perpendicular to the guiding groove part 132 of the movable base 13, and a height of the guiding groove part 132 of the movable base 13 is higher than a height of the rail part 131 of the movable base 13. The rail part 131 includes a rail 133 disposed on a top of the movable base 13, the guiding groove part 132 includes a second guiding groove 134 disposed on a bottom of the movable base 13, the rail part 131 of the movable base 13 is assembled with the first guiding grooves 122 of the first arc-shaped rack 12, and the movable base 13 of the clamping device 10 is movable relative to the first arc-shaped rack 12 of the clamping device 10.

The second arc-shaped rack 14 of the clamping device 10 includes a second rack 141 disposed on an inner side thereof. The second arc-shaped rack 14 of the clamping device 10 can be made by ceramic or polymer, but these examples are merely for exemplary illustration, and the application field of the present invention is not limited thereto. The second arc-shaped rack 14 of the clamping device 10 is assembled with the second guiding groove 134 of the guiding groove part 132, so that the second arc-shaped rack 14 of the clamping device 10 is movable relative to the movable base 13 of the clamping device 10.

The first motor 15 of the clamping device 10 is fixed on the motor fixing part 111 of the base 11. In an embodiment, the first motor 15 of the clamping device 10 can be a DC motor or a stepper motor, but these examples are merely for exemplary illustration, and the application field of the present invention is not limited thereto. The first motor 15 of the clamping device 10 can be operated to rotate the base 11, that is, the first motor 15 of the clamping device 10 can be used to rotate the whole clamping device 10.

The second motor 16 of the clamping device 10 includes a second gear 161. In an embodiment, the second motor 16 of the clamping device 10 can be a DC motor or a stepper motor, but these examples are merely for exemplary illustration, and the application field of the present invention is not limited thereto. The second motor 16 of the clamping device 10 can be fixed on the rail part 131 of the movable base 13 by a screwing manner, and the second gear 161 of the second motor 16 is assembled with the first rack 123 of the first arc-shaped rack 12.

Particularly, an end of the rail part 131 of the movable base 13 protruded out of the guiding groove part 132 of the movable base 13 is configured to fix with the second motor 16 of the clamping device 10, and the end has an opening formed on a bottom thereof and corresponding in position to the first rack 123 of the first arc-shaped rack 12, so that the second gear 161 of the second motor 16 can be assembled with the first rack 123 of the first arc-shaped rack 12 through the opening.

The third motor 17 of the clamping device 10 includes a third gear 171. In an embodiment, the third motor 17 of the clamping device 10 can be a DC motor or a stepper motor, but these examples are merely for exemplary illustration, and the application field of the present invention is not limited thereto. The third motor 17 of the clamping device 10 can be fixed on the guiding groove part 132 of the movable base 13 by a screwing manner, and the third gear 171 of the third motor 17 is assembled with the second rack 141 of the second arc-shaped rack 14.

Particularly, an end of the guiding groove part 132 of the movable base 13 protruded out of the rail part 131 of the guiding groove part 132 of the movable base 13 is configured to fix with the third motor 17 of the clamping device 10, and the end has an opening formed on a bottom thereof and corresponding in position to the second rack 141 of the second arc-shaped rack 14, so that the third gear 171 of the third motor 17 can be assembled with the second rack 141 of the second arc-shaped rack 14 through the opening.

The first clamping rod 18 of the clamping device 10 includes a first fixing end 181 and a first clamping assembly 182. In an embodiment, the first clamping rod 18 of the clamping device 10 can be made by ceramic or polymer, but these examples are merely for exemplary illustration, and the application field of the present invention is not limited thereto. The first fixing end 181 of the first clamping rod 18 is fixed on the first end of the second arc-shaped rack 14.

The second clamping rod 19 of the clamping device 10 includes a second fixing end 191 and a second clamping assembly 192. In an embodiment, the second clamping rod 19 of the clamping device 10 can be made by ceramic or polymer, but these examples are merely for exemplary illustration, and the application field of the present invention is not limited thereto. The second fixing end 191 of the second clamping rod 19 is fixed on a second end of the second arc-shaped rack 14.

The first clamping assembly 182 of the clamping device 10 and the second clamping assembly 192 of the clamping device 10 are configured to clamp the ultrasonic detection device 30, that is, the ultrasonic detection device 30 can be assembled with the first clamping assembly 182 of the clamping device 10 and the second clamping assembly 192 of the clamping device 10 by a screwing manner, so as to be clamped between the first clamping assembly 182 of the clamping device 10 and the second clamping assembly 192 of the clamping device 10.

Figure 2A:
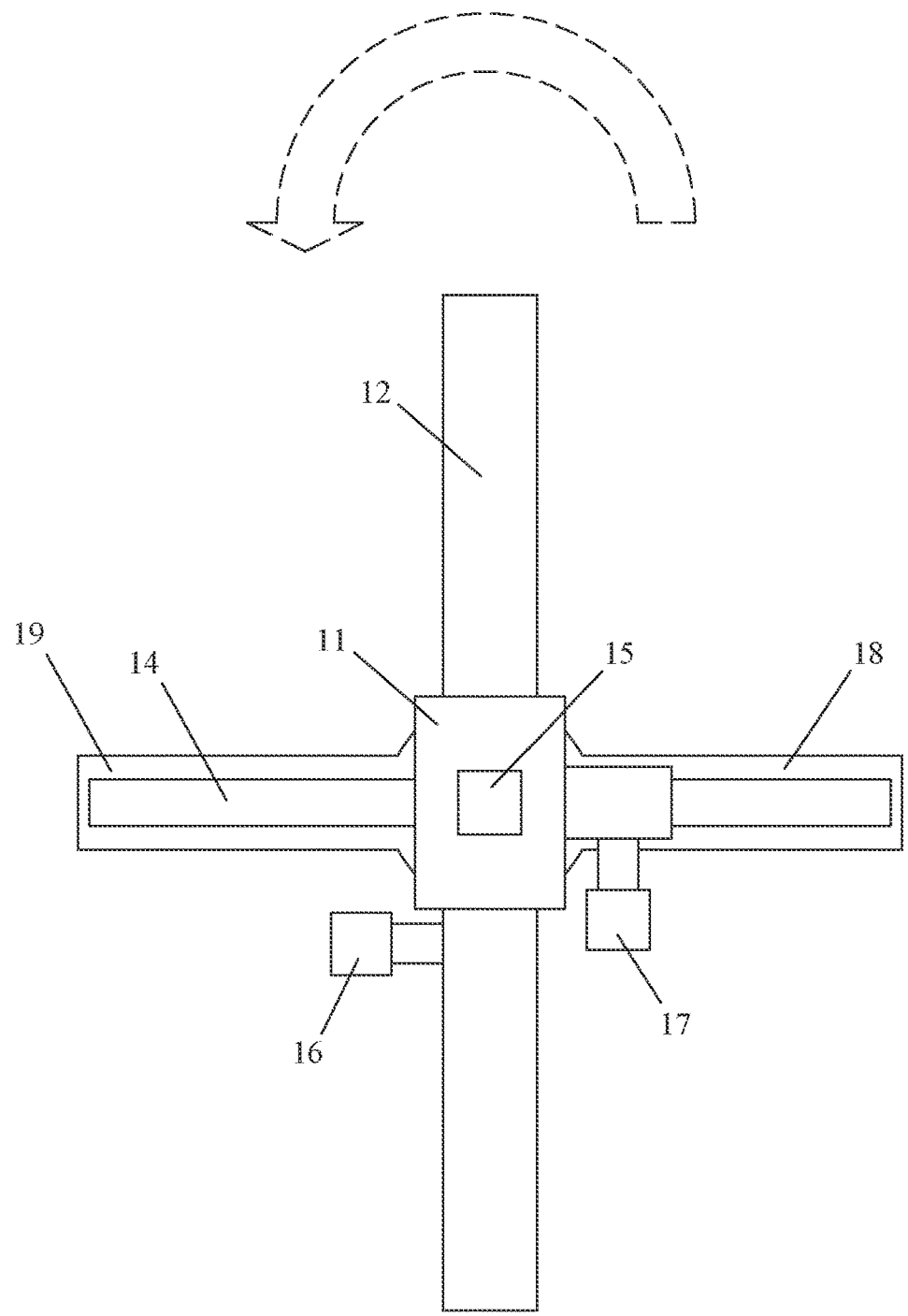
FIG. 2A is a plan view of a clamping device of the present invention at an original position.
Figure 2B:
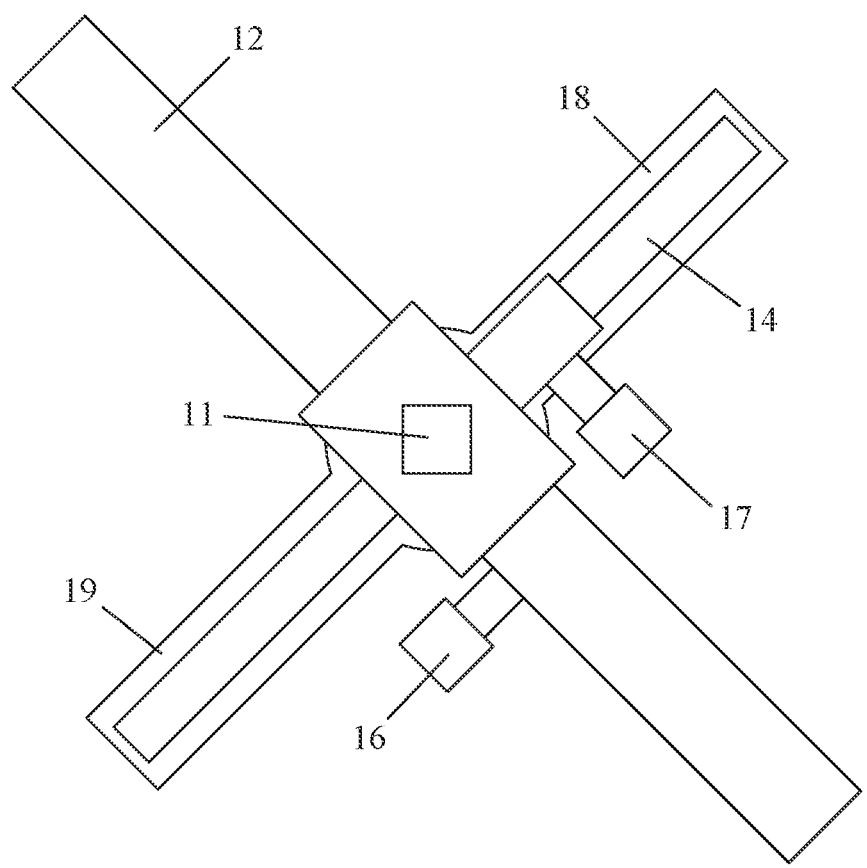
FIG. 2B is a plan view of the clamping device of the present invention after being rotated.

The remote control device 20 can be used to remotely control the first motor 15 of the clamping device 10, to control a rotational position of the base 11 of the clamping device 10, that is, the first motor 15 of the clamping device 10 can be remotely controlled to control the rotational position of the ultrasonic detection device 30. Please refer to FIGS. 2A and 2B, FIG. 2A is a plan view of the clamping device of the present invention at an original, and FIG. 2B is a plan view of the clamping device after being rotated. As shown in FIG. 2A, the remote control device 20 controls the first motor 15 of the clamping device 10, to drive the base 11 of the clamping device 10 to counter-clockwise rotate, and a rotational result of the above-mentioned control operation is shown in FIG. 2B. The dashed arrow of FIG. 2A schematically shows the rotational direction, but the present invention is not limited thereto.

Figure 3A:
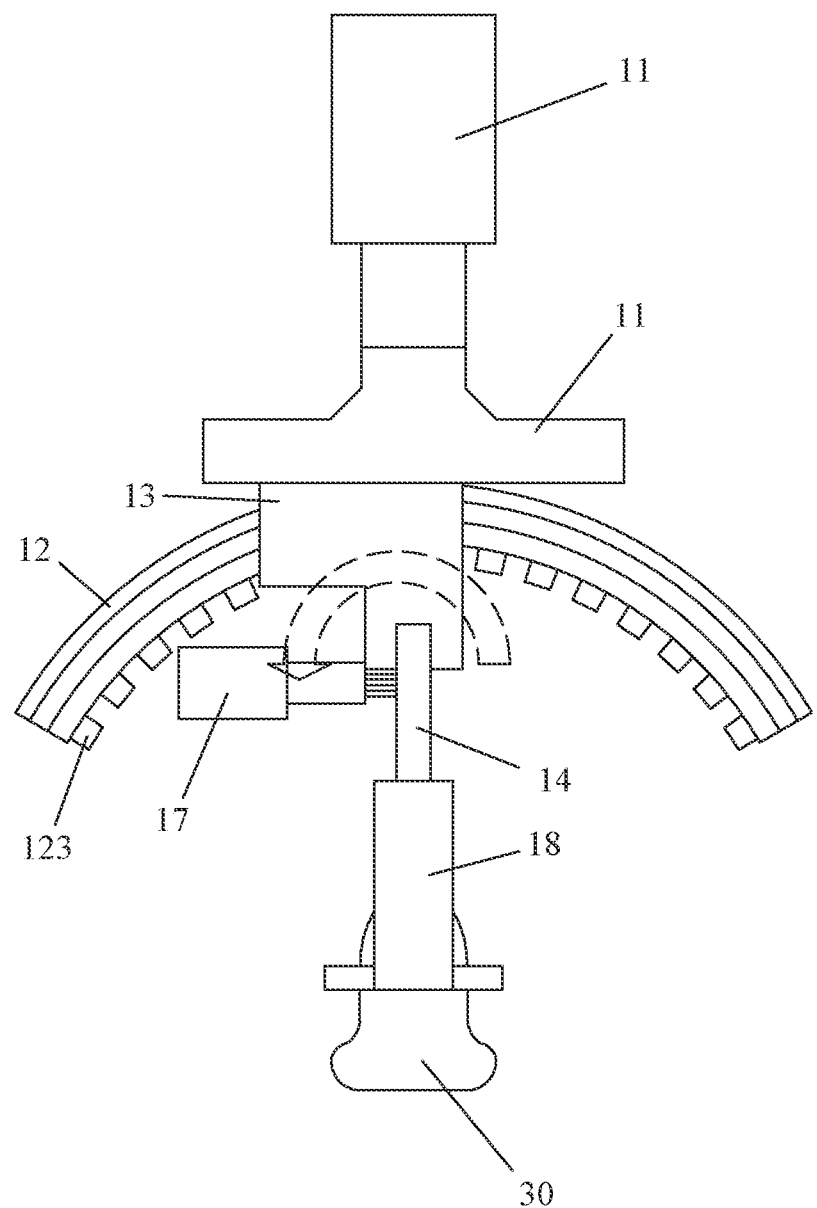
FIG. 3A is a plan view of a movable base of a clamping device of the present invention at an original position.
Figure 3B:
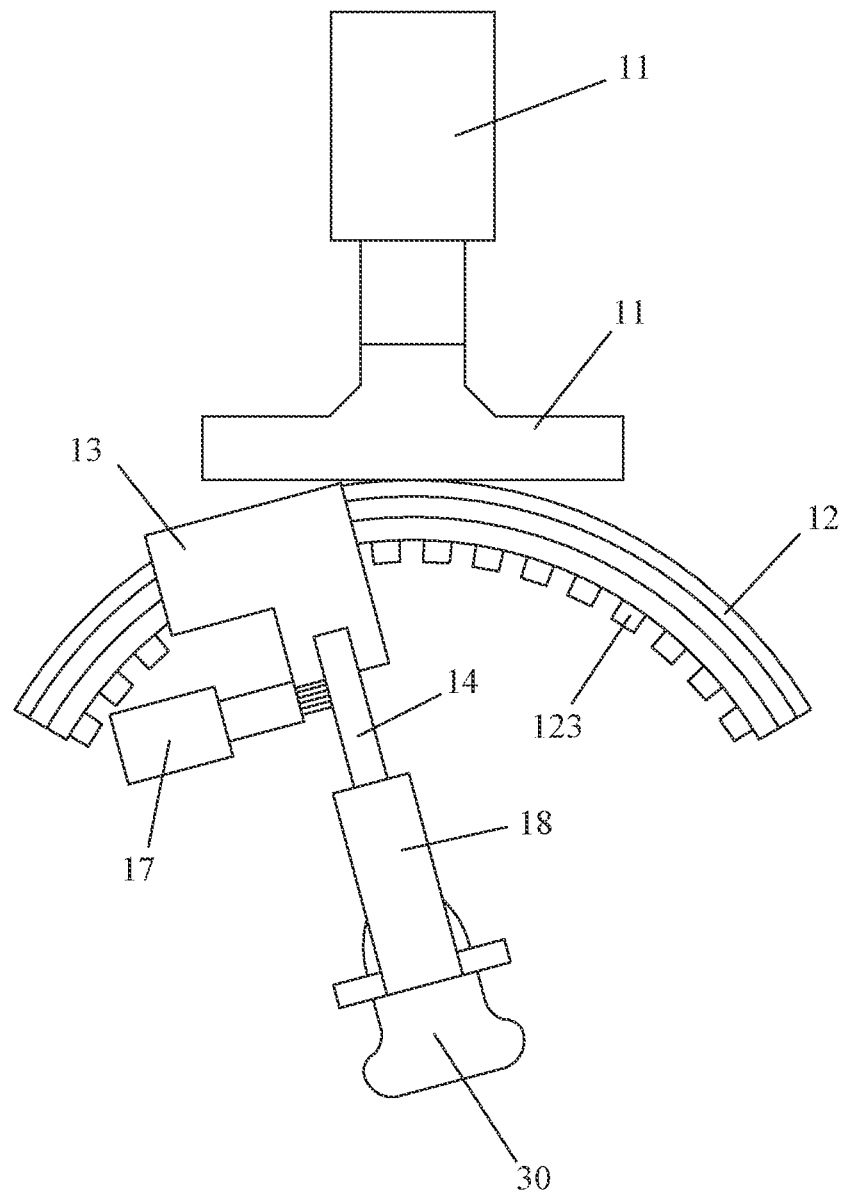
FIG. 3B is a plan view of a movable base of the clamping device of the present invention after being moved.

The remote control device 20 can be used to remotely control the second motor 16 of the clamping device 10, to control a moving position of the movable base 13 of the clamping device 10 relative to the first arc-shaped rack 12 of the clamping device 10. Please refer to FIGS. 3A and 3B. FIG. 3A is a plan view of a movable base of a clamping device of the present invention at an original position, and FIG. 3B is a plan view of the movable base of the clamping device after being moved. As shown in FIG. 3A, the remote control device 20 controls the second motor 16 of the clamping device 10, to drive the movable base 13 of the clamping device 10 to counter-clockwise rotate, and a rotational result of the above-mentioned control operation is shown in FIG. 3B. The dashed arrow of FIG. 3A schematically shows the rotational direction, but the present invention is not limited thereto.

Figure 4A:
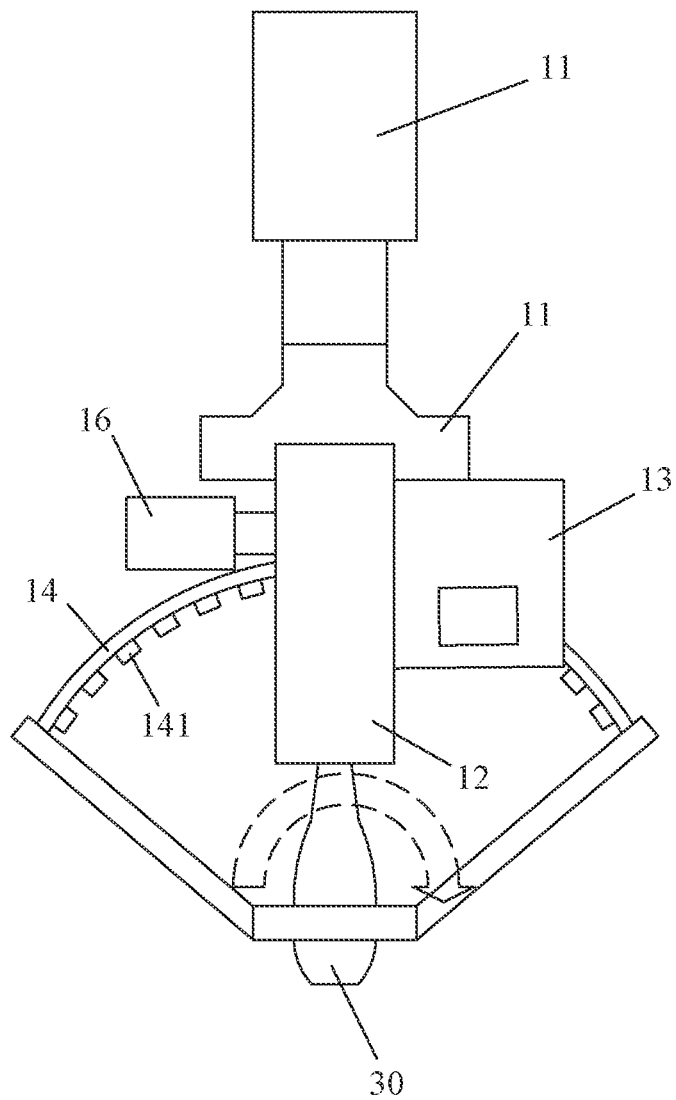
FIG. 4A is a plan view of a second arc-shaped rack of a clamping device of the present invention at an original position.
Figure 4B:
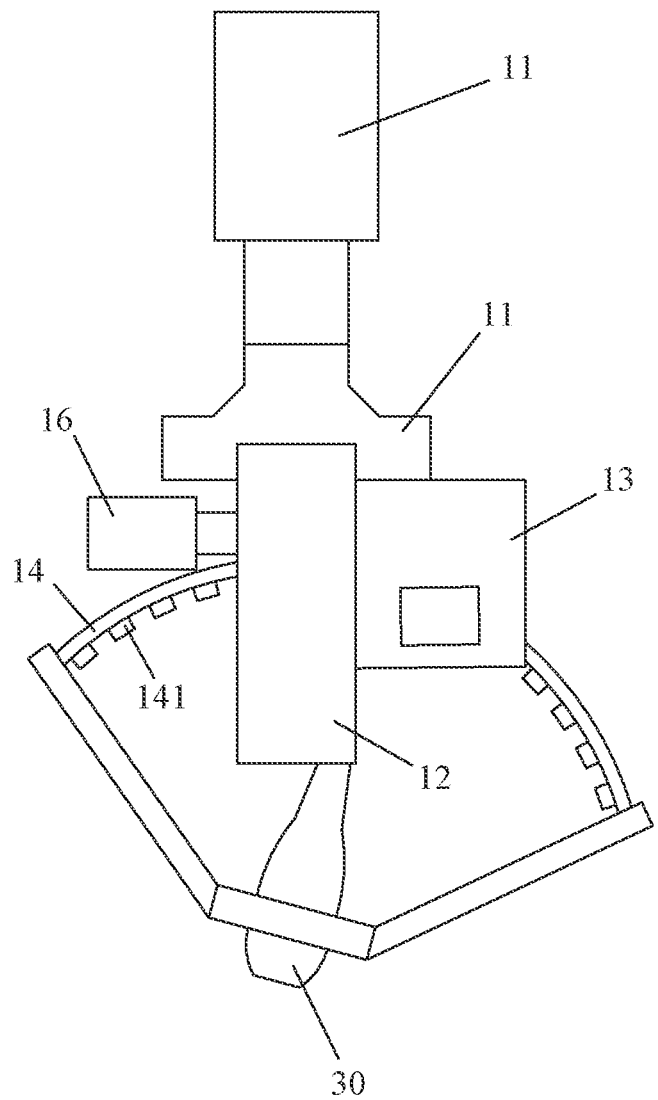
FIG. 4B is a plan view of a second arc-shaped rack of the clamping device of the present invention after being moved.

The remote control device 20 can be used to remotely control the third motor 17 of the clamping device 10, to control the moving position of the second arc-shaped rack 14 of the clamping device 10 relative to the movable base 13 of the clamping device 10. Please refer to FIGS. 4A and 4B. FIG. 4A is a plan view of a second arc-shaped rack of a clamping device of the present invention at an original position, and FIG. 4B is a plan view of the second arc-shaped rack of the clamping device after being moved. As shown in FIG. 4A, the remote control device 20 controls the third motor 17 of the clamping device 10, to drive the second arc-shaped rack 14 of the clamping device 10 to clockwise rotate, and a rotational result of the above-mentioned control operation is shown in FIG. 4B. The dashed arrow of FIG. 4A schematically shows the rotational direction, but the present invention is not limited thereto.

According to the contents shown in FIGS. 2A to 4B, the remote controls performed on the first motor 15 of the clamping device 10, the second motor 16 of the clamping device 10 and the third motor 17 of the clamping device 10, by the remote control device 20, can be appropriately combined, so that an accurate three-dimensional detection angle can be provided to the ultrasonic detection device 30 for ultrasonic detection by means of remotely controlling the clamping device 10 by the remote control device 20.

It should be noted that, in order to provide the accurate three-dimensional detection angle to the ultrasonic detection device 30 for ultrasonic detection, a perpendicular bisector of the base 11 of the clamping device 10 must pass through a central point of a front edge of the ultrasonic detection device 30, a central position of the first arc-shaped rack 12 of the clamping device 10 must be a central point of the front edge of the ultrasonic detection device 30, and a central position of the second arc-shaped rack 14 of the clamping device 10 must be a central point of the front edge of the ultrasonic detection device 30.

According to above-mentioned contents, the difference between the present invention and the conventional technology is that the remote control device of the clamping apparatus of the present invention is used for remotely controlling the first motor to control the rotational position of the base, for remotely controlling the second motor to control the moving position of the movable base relative to the first arc-shaped rack, and for remotely controlling the third motor to control the moving position of the second arc-shaped rack relative to the movable base.

Therefore, the technical solution of the present invention is able to solve the conventional technology problem that the conventional ultrasonic detection equipment is inconvenient in operation, to achieve the technical effect of providing the accurate three-dimensional detection angle to the ultrasonic detection device.

The present invention disclosed herein has been described by means of specific embodiments. However, numerous modifications, variations and enhancements can be made thereto by those skilled in the art without departing from the spirit and scope of the disclosure set forth in the claims.

What is claimed is:

1. A clamping apparatus for an ultrasonic detection device, comprising: a clamping device comprising: a base comprising a motor fixing part and a base fixing part; a first arc-shaped rack comprising a rack fixing part, a set of first guiding grooves, and a first rack, wherein the rack fixing part is fixed with the base fixing part, and the first rack is disposed on an inner side of the first arc-shaped rack; a movable base comprising a rail part and a guiding groove part, wherein the rail part is disposed in perpendicular to the guiding groove part, the rail part comprises a rail disposed on a top of the movable base, the guiding groove part comprises a second guiding groove disposed on a bottom of the movable base, and the rail part is assembled with the first guiding grooves; a second arc-shaped rack comprising a second rack disposed on an inner side thereof, wherein the second arc-shaped rack is assembled with the second guiding groove; a first motor fixed on the motor fixing part; a second motor comprising a second gear, wherein the second motor is fixed on the rail part, and the second gear is assembled with the first rack; a third motor comprising a third gear, wherein the third motor is fixed on the guiding groove part, and the third gear is assembled with the second rack; a first clamping rod comprising a first fixing end and a first clamping assembly, wherein the first fixing end is fixed on a first end of the second arc-shaped rack; and a second clamping rod comprising a second fixing end and a second clamping assembly, wherein the second fixing end is fixed on a second end of the second arc-shaped rack;

wherein the first clamping assembly and the second clamping assembly are configured to clamp the ultrasonic detection device; and a remote control device configured to remotely control the first motor to control a rotational position of the base, remotely control the second motor to control a moving position of the movable base relative to the first arc-shaped rack, and remotely control the third motor to control a moving position of the second arc-shaped rack relative to the movable base, so as to provide a three-dimensional detection angle to the ultrasonic detection device.

2. The clamping apparatus for ultrasonic detection device according to claim 1, wherein a perpendicular bisector of the base passes through a central point of a front edge of the ultrasonic detection device.

3. The clamping apparatus for ultrasonic detection device according to claim 1, wherein a central position of the first arc-shaped rack is at a central point of a front edge of the ultrasonic detection device.

4. The clamping apparatus for ultrasonic detection device according to claim 1, wherein a central position of the second arc-shaped rack is at a central point of a front edge of the ultrasonic detection device.

5. The clamping apparatus for ultrasonic detection device according to claim 1, wherein the ultrasonic detection device is assembled with the first clamping assembly and the second clamping assembly by a screwing manner, so as to be clamped between the first clamping assembly and the second clamping assembly.

6. The clamping apparatus for ultrasonic detection device according to claim 1, wherein the second motor is fixed on the rail part by a screwing manner.

7. The clamping apparatus for ultrasonic detection device according to claim 1, wherein the third motor is fixed on the guiding groove part by a screwing manner.

8. The clamping apparatus for ultrasonic detection device according to claim 1, wherein a height of the guiding groove part is greater than a height of the rail part.

9. The clamping apparatus for ultrasonic detection device according to claim 1, wherein an end of the rail part protruded out of the guiding groove part is configured to fix with the second motor, and the end has an opening formed on a bottom thereof and corresponding in position to the first rack, and the second gear is assembled with the first rack through the opening.

10. The clamping apparatus for ultrasonic detection device according to claim 1, wherein an end of the guiding groove part protruded out of the rail part is configured to fix with the third motor, and the end has an opening formed on a bottom thereof and corresponding in position to the second rack, and the third gear is assembled with the second rack through the opening.

* * * * *